(12) United States Patent
Terwey

(10) Patent No.: US 11,420,020 B2
(45) Date of Patent: Aug. 23, 2022

(54) MEDICAL DEVICE INCLUDING A VARIABLE TORQUE ASSEMBLY FOR DEVICE DEFLECTION

(71) Applicant: St. Jude Medical, Cardiology Division, Inc., St. Paul, MN (US)

(72) Inventor: Russell David Terwey, Saint Michael, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 239 days.

(21) Appl. No.: 16/681,612

(22) Filed: Nov. 12, 2019

(65) Prior Publication Data
US 2020/0139083 A1 May 7, 2020

Related U.S. Application Data

(63) Continuation of application No. 15/145,179, filed on May 3, 2016, now Pat. No. 10,507,303.
(Continued)

(51) Int. Cl.
*A61M 25/01* (2006.01)
*A61B 17/00* (2006.01)
*A61B 1/005* (2006.01)

(52) U.S. Cl.
CPC ... *A61M 25/0147* (2013.01); *A61B 17/00234* (2013.01); *A61M 25/0136* (2013.01);
(Continued)

(58) Field of Classification Search
CPC .......... A61M 25/0136; A61M 25/0147; A61M 25/0133; A61B 1/0052
See application file for complete search history.

(56) References Cited

U.S. PATENT DOCUMENTS

| 5,549,542 A | 8/1996 | Kovalcheck |
| 5,938,616 A | 8/1999 | Eaton et al. |

(Continued)

FOREIGN PATENT DOCUMENTS

| CN | 101708130 A | 5/2010 |
| EP | 1607118 A1 | 12/2005 |

(Continued)

OTHER PUBLICATIONS

International Search Report and Written Opinion for PCT Application No. PCT/US2016/030509, dated Jul. 15, 2016, 19 pages.

*Primary Examiner* — Emily L Schmidt
(74) *Attorney, Agent, or Firm* — Armstrong Teasdale LLP

(57) ABSTRACT

The present disclosure provides a medical device comprising a deflecting assembly configured to assist in deflecting a distal portion of a catheter shaft. The deflecting assembly may include a first rotatable member having a first diameter and a first pull wire coupled thereto and a second rotatable member having a second diameter smaller than the first diameter and a second pull wire coupled thereto, wherein the second rotatable member is coupled to the first rotatable member such that a center point of the second rotatable member is offset from a center point of the first rotatable member. The first and second rotatable members are configured such that rotation of the first rotatable member via the first pull wire causes rotation of the second rotatable member and second pull wire, thus resulting in deflection of a distal portion of the medical device.

13 Claims, 4 Drawing Sheets

Related U.S. Application Data

(60) Provisional application No. 62/158,154, filed on May 7, 2015.

(52) U.S. Cl.
CPC ... *A61B 1/0052* (2013.01); *A61B 2017/00323* (2013.01); *A61B 2017/00327* (2013.01)

(56) References Cited

U.S. PATENT DOCUMENTS

| | | |
|---|---|---|
| 8,808,166 B2 | 8/2014 | Hosaka |
| 2007/0221701 A1 | 9/2007 | Ortiz et al. |
| 2008/0139886 A1 | 6/2008 | Tatsuyama |
| 2014/0121462 A1 | 5/2014 | Okamoto |
| 2015/0094654 A1 | 4/2015 | Bansal et al. |

FOREIGN PATENT DOCUMENTS

| | | |
|---|---|---|
| JP | 2008-142199 A | 6/2006 |
| JP | 4323210 B2 | 9/2009 |

MEDICAL DEVICE INCLUDING A VARIABLE TORQUE ASSEMBLY FOR DEVICE DEFLECTION

A. CROSS-REFERENCE TO RELATED APPLICATIONS

This application is a continuation application of U.S. patent application Ser. No. 15/145,179, filed May 3, 2016, entitled "MEDICAL DEVICE INCLUDING A VARIABLE TORQUE ASSEMBLY FOR DEVICE DEFLECTION," which claims the benefit of priority to U.S. Provisional Patent Application No. 62/158,154, filed May 7, 2015, entitled "MEDICAL DEVICE INCLUDING A VARIABLE TORQUE ASSEMBLY FOR DEVICE DEFLECTION," the entire contents and disclosure of which are hereby incorporated by reference in their entirety.

B. FIELD OF THE DISCLOSURE

The present disclosure relates generally to medical devices that are used in the human body. In particular, in many embodiments, the present disclosure relates to a medical device deflecting assembly including a variable torque assembly for assisting in deflecting a distal region of a catheter shaft.

C. BACKGROUND

Medical devices, such as catheter systems, are well known in the art for use in medical procedures, such as diagnostic (e.g., cardiac mapping) and therapeutic procedures (e.g., cardiac ablation). Typical catheter systems generally include an elongated flexible catheter shaft extending from a control handle containing an actuating mechanism. A physician manipulates the catheter shaft through the patient's vasculature to an intended site within the patient via the actuating mechanism contained within the control handle.

An actuating mechanism of the catheter system may include mechanical steering features or components that may be manually manipulated to position a catheter shaft within the body at a desired site or to operate the catheter system during use. In some embodiments, a catheter or catheter system may be positioned within a patient's vasculature during a procedure by simultaneous application of torque or force at the proximal end of the catheter and/or by selectively deflecting the distal tip of the catheter in a desired direction.

The distal tip of the catheter can be deflected by a pull wire or other tension member attached or anchored at the distal end of the catheter and extending proximally to an actuator in a control handle that controls the application of tension on the pull wire. Distal movement of the catheter shaft with respect to a body of the control handle, upon the application of an external force on the actuating mechanism, may impose eccentric pull forces on the distal portion of the catheter shaft resulting in the distal portion of the catheter shaft assuming a deflected configuration. Absent an external force exerted on the actuating mechanism, the catheter shaft tends to return to its natural, unstressed position due to the force exerted on it by the strained pull wire.

BRIEF SUMMARY OF THE DISCLOSURE

Catheter systems of the multiple embodiments of the present disclosure include a deflecting assembly that exhibits an increased mechanical advantage during deflection of the distal region of the catheter shaft as compared to traditional flexible catheters without the presently disclosed deflecting assembly; that is, the present disclosure provides embodiments of catheter systems wherein the overall force needed to advance a plunger distally with respect to the handle of the device, and thus cause deflection of the distal portion of the catheter shaft, is reduced as compared to medical devices that do not include the disclosed deflecting assembly. In many embodiments, the force required to achieve the desired deflection remains substantially constant throughout the entire deflection. These force reductions provide an improved catheter system that provides increased performance in a consistent manner.

In one embodiment, the present disclosure is directed to an assembly for use in deflecting a portion of a medical device. The assembly comprises a first rotatable member having a first diameter and a first pull wire coupled thereto and a second rotatable member having a second diameter smaller than the first diameter and a second pull wire coupled thereto. The second rotatable member is coupled to the first rotatable member such that a center point of the second rotatable member is offset from a center point of the first rotatable member, and the first and second rotatable members are configured such that rotation of the first rotatable member via the first pull wire causes rotation of the second rotatable member and second pull wire resulting in deflection of a distal end of the medical device.

In another embodiment, the present disclosure is directed to a medical device comprising a catheter shaft, a handle, and a deflecting assembly. The catheter shaft has a proximal end and a deflectable distal region, and the handle is coupled to the proximal end of the catheter shaft. The handle includes a plunger movable relative to the handle along a longitudinal axis. The deflecting assembly comprises a first rotatable member coupled to the plunger via a first pull wire and having a first diameter, and a second rotatable member coupled to the deflectable distal region via a second pull wire and having a second diameter smaller than the first diameter. The second rotatable member is coupled to the first rotatable member such that a center point of the second rotatable member is offset from a center point of the first rotatable member. The deflecting assembly is configured such that distal movement of the plunger effects rotational movement in a first direction of the first rotatable member and the second rotatable member resulting in deflection of the deflectable distal region of the catheter shaft.

In another embodiment, the present disclosure is directed to a method of deflecting a distal region of a medical device. The method comprises providing a medical device comprising a catheter shaft, a handle, and a deflecting assembly. The catheter shaft has a proximal end and a deflectable distal region. The handle is coupled to the proximal end of the catheter shaft and includes a plunger movable relative to the handle along a longitudinal axis. The deflecting assembly comprises a first rotatable member coupled to the plunger via a first pull wire and a second rotatable member coupled to the deflectable distal region via a second pull wire. The second rotatable member is coupled to the first rotatable member such that a center point of the second rotatable member is offset from a center point of the first rotatable member. The method further comprises distally advancing the plunger with respect to the handle to a position wherein the deflectable distal region of the catheter shaft is in a deflected configuration.

The foregoing and other aspects, features, details, utilities and advantages of the present disclosure will be apparent

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

Figure 1:
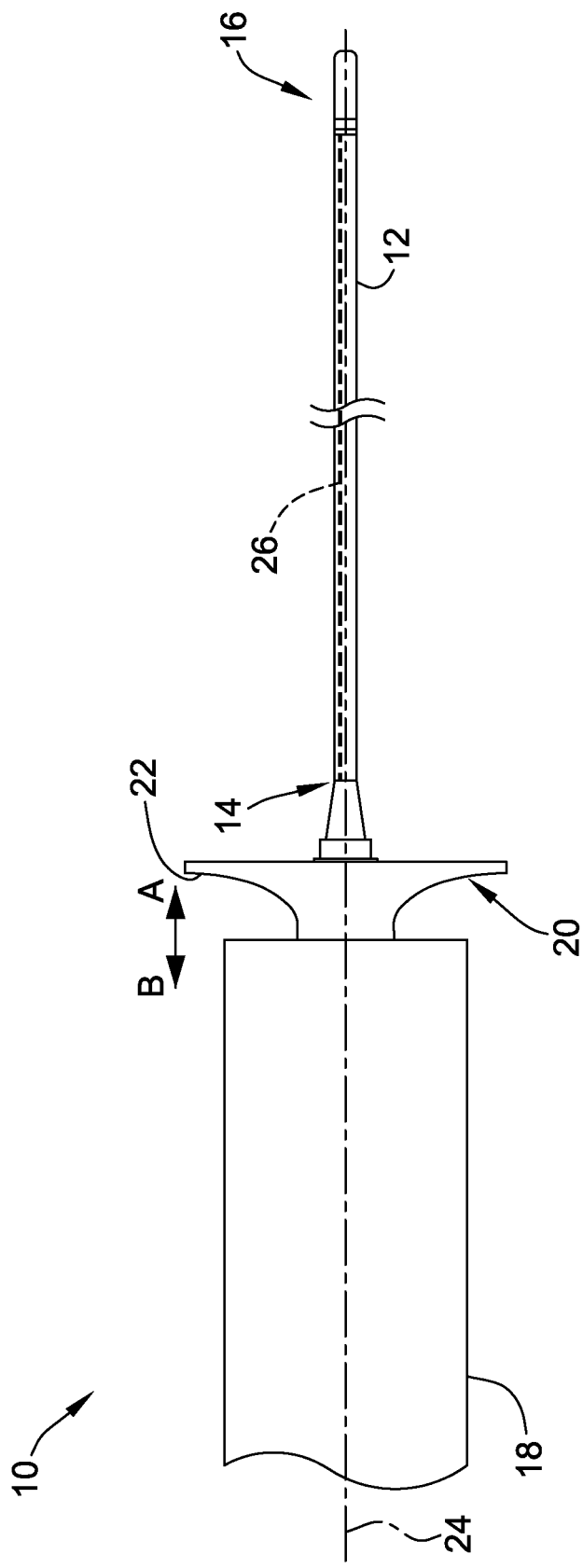
FIG. 1 is a perspective view of one embodiment of a catheter system including a handle, a catheter shaft, and an actuating mechanism.

The present disclosure provides catheter systems suitable for use in navigating the human vasculature for various known medical procedures. Catheter systems of the multiple embodiments of the present disclosure include a novel deflecting assembly that exhibits an increased mechanical advantage during deflection of the distal region of the catheter shaft as compared to traditional flexible catheters without the presently disclosed deflecting assembly; that is, the present disclosure provides embodiments of catheter systems wherein the overall force needed to advance an actuator or plunger distally with respect to the handle of the catheter device, and thus cause deflection of the distal portion of the catheter shaft, is reduced as compared to medical devices that do not include the disclosed deflecting assembly. Such disclosed embodiments may lead to more consistent and improved patient outcomes and reduced stress on a user. For purposes of this description, the present disclosure will be described in connection with numerous embodiments of a uni-directional plunger-type catheter, including a deflecting assembly. It is contemplated, however, that one or more of the described features and methods of the present disclosure as described herein may be incorporated into any number of catheters or other medical devices as would be appreciated by one of ordinary skill in the art based on the disclosure herein.

More specifically, some embodiments of the present disclosure provide a catheter system including a deflecting assembly comprising a first rotatable member having a first pull wire coupled thereto and a second rotatable member having a second, separate, pull wire coupled thereto. The second rotatable member is coupled to the first rotatable member such that a center point of the second rotatable member is offset from a center point of the first rotatable member; that is, the first and second rotatable members are coupled to one another in a stacked configuration, but such that the center points of the first and second rotatable members are not vertically aligned with one another. In many embodiments, the second rotatable member has a diameter that is smaller than that of the first rotatable member. The first pull wire is coupled to an actuator, or plunger, of the catheter system, and the second pull wire is coupled to the deflectable distal region of the catheter shaft. During use, the actuator is distally advanced with respect to the handle, thus causing rotation of the first rotatable member, which in turn causes rotation of the second rotatable member in the same direction. Rotation of the second rotatable member causes the second pull wire to wrap around the second rotatable member, and thus causes deflection of the distal region of the catheter shaft. In some embodiments described herein, an additional pull wire may be further utilized to assist in returning the deflected distal region of the catheter shaft back to a straight, undeflected position.

The deflecting assembly as described herein provides an increased mechanical advantage as opposed to catheter systems that do not include the presently disclosed deflecting assembly, but rather include, for example, a single pull or deflection wire for effecting deflection of the distal region of the catheter shaft. That is, catheter systems including a deflectable catheter shaft known in the art oftentimes utilize an eccentric pull wire configured to interact with an actuator via a catheter shaft in order to initiate the deflection of the distal region of the catheter shaft. As discussed in greater detail below, during use of catheter systems such as these, a user may advance an actuator (also referred to as a plunger or actuator lever) distally, thus causing a proximal end of the pull wire, which may be mounted or fastened to a gripper, to move along with the catheter shaft until such movement is stopped or prohibited by an obstacle (or shoulder) positioned within the handle housing. Continued distal movement of the catheter shaft, driven by the drive lever, creates a high tension on the pull wire. Due to the eccentric fixation of the pull wire to the distal end of the catheter shaft, the tension on the pull wire generates the bending moment imposed on the distal region of the catheter shaft, leading to deflection of the distal region of the catheter shaft. The force exerted by the user to deflect the distal region of the catheter shaft, however, can potentially in some circumstances become tiresome during a procedure.

By utilizing the presently disclosed deflecting assembly, a variable torque is created on the pull wire, thus reducing the amount of force needed to deflect the distal region of the catheter shaft. That is, as the actuator is distally advanced, the first pull wire causes rotation of the first rotatable member which thus causes rotation of the second rotatable member in the same direction. Because the second rotatable member is coupled to the first rotatable member in an offset position, the second pull wire moves from a position farthest away from the center point of the first rotatable member when the deflectable distal region is in a neutral state to a position closer to the center point of the first rotatable member when the deflectable distal region is in a deflected state, thus increasing the torque as the distal region of the catheter is deflected and limiting additional force required by the user to continue deflection of the distal region of the catheter shaft. By providing a deflecting assembly that utilizes a variable torque on the pull wire causing deflection of the distal region of the catheter shaft (i.e., an increased torque as the distal region is deflected), an increased mechanical advantage can be achieved, thus reducing the amount of overall force required to cause deflection of the distal region of the catheter shaft. That is, the amount of force on the user does not substantially increase as the actuator is distally advanced through full deflection of the distal region of the catheter shaft. This may result in reduced fatigue for the user over time.

Figure 2:
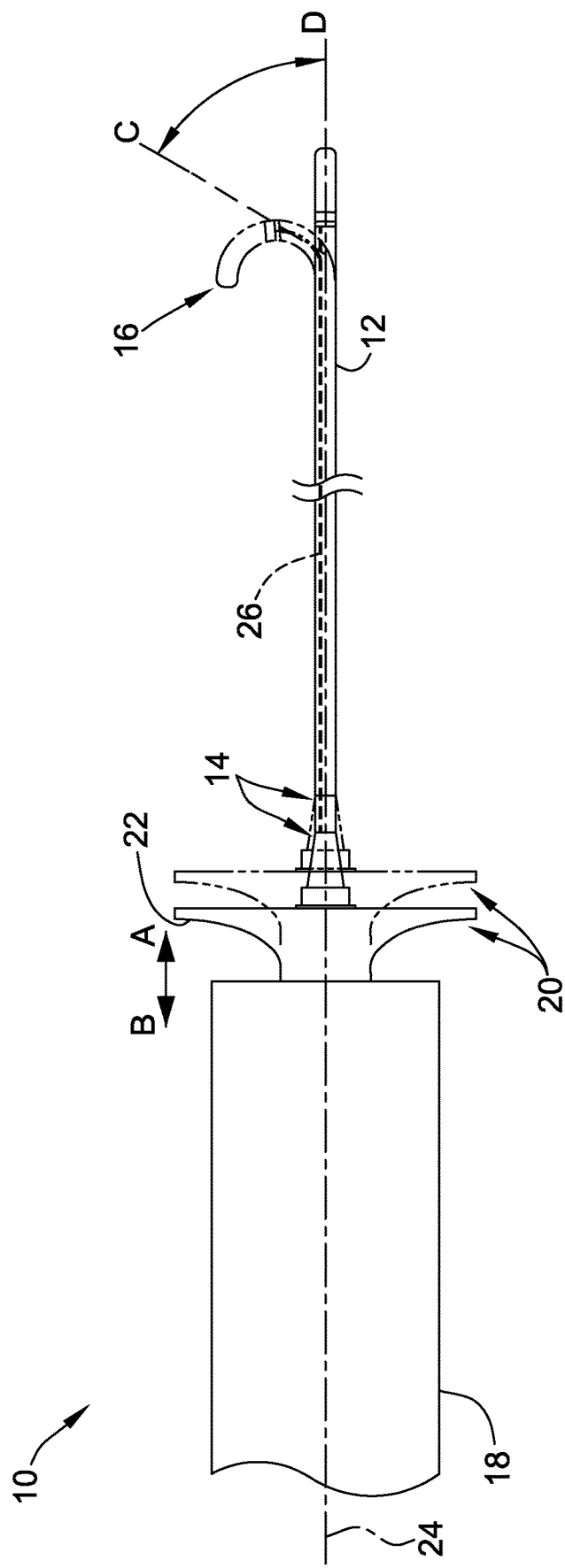
FIG. 2 illustrates the use of a pull wire to deflect the distal end of the catheter shaft of FIG. 1.

Referring now to the drawings, and specifically to FIG. 1, there is shown a plunger-type catheter 10 in an undeflected, or neutral position. Catheter 10 generally includes a catheter shaft 12, having a proximal region 14 and a deflectable distal region 16, a handle 18, and an actuator housing (not shown) located within handle 18. Handle 18 includes an actuator mechanism 20. As illustrated in FIGS. 1 and 2, actuator mechanism 20 includes an drive lever 22 (also referred to as an actuator lever or plunger) that is moveable relative to handle 18 along a central, longitudinal axis 24 of handle 18 in a first direction along arrow A (e.g., distally) that effects deflection of distal region 16 of catheter shaft 12 from the neutral position, as well as in a second, opposite direction along arrow B (e.g., proximally) that effects return or retraction of distal region 16 toward the neutral position. For example, catheter 10 can be similar to the type disclosed in U.S. Provisional Application No. 61/884,897, filed Sep. 30, 2013, which is hereby incorporated by reference as though fully set forth herein.

FIG. 2 illustrates the use of a pull wire 26 for deflecting distal region 16 of catheter shaft 12. Pull wire 26 extends through a lumen of catheter shaft 12. Pull wire 26 is coupled to a pull ring (not shown) embedded in distal region 16 of catheter shaft 12 and to a gripper (not shown) in handle 18, such that movement of drive lever 22 in the first direction along arrow A effects deflection of distal region 16 of catheter shaft 12 from the neutral position along a first deflection direction (e.g., arrow C), and such that movement of drive lever 22 in the second direction along arrow B effects the return or retraction of distal region 16 of catheter shaft 12 towards the neutral position (e.g., along arrow D). Insofar as a person of ordinary skill in the art will appreciate the use of pull wires in a catheter, a detailed explanation of this aspect of the disclosure is not provided herein.

Although the catheter systems disclosed herein are described primarily with respect to unidirectional catheters, it should be recognized that the disclosed principles are equally applicable in other contexts, including but not limited to, bidirectional catheters. That is, for example, with various structural arrangements of the restraining assembly discussed below, movement of drive lever 22 in the first direction along arrow A could affect deflection of distal region 16 from the neutral position in a first defection direction (e.g., arrow C in FIG. 2), while movement of drive lever 22 in the second direction could affect deflection of distal region 16 from the neutral position in a second deflection direction, with both the first and second deflection directions lying in the same plane.

Figure 3:
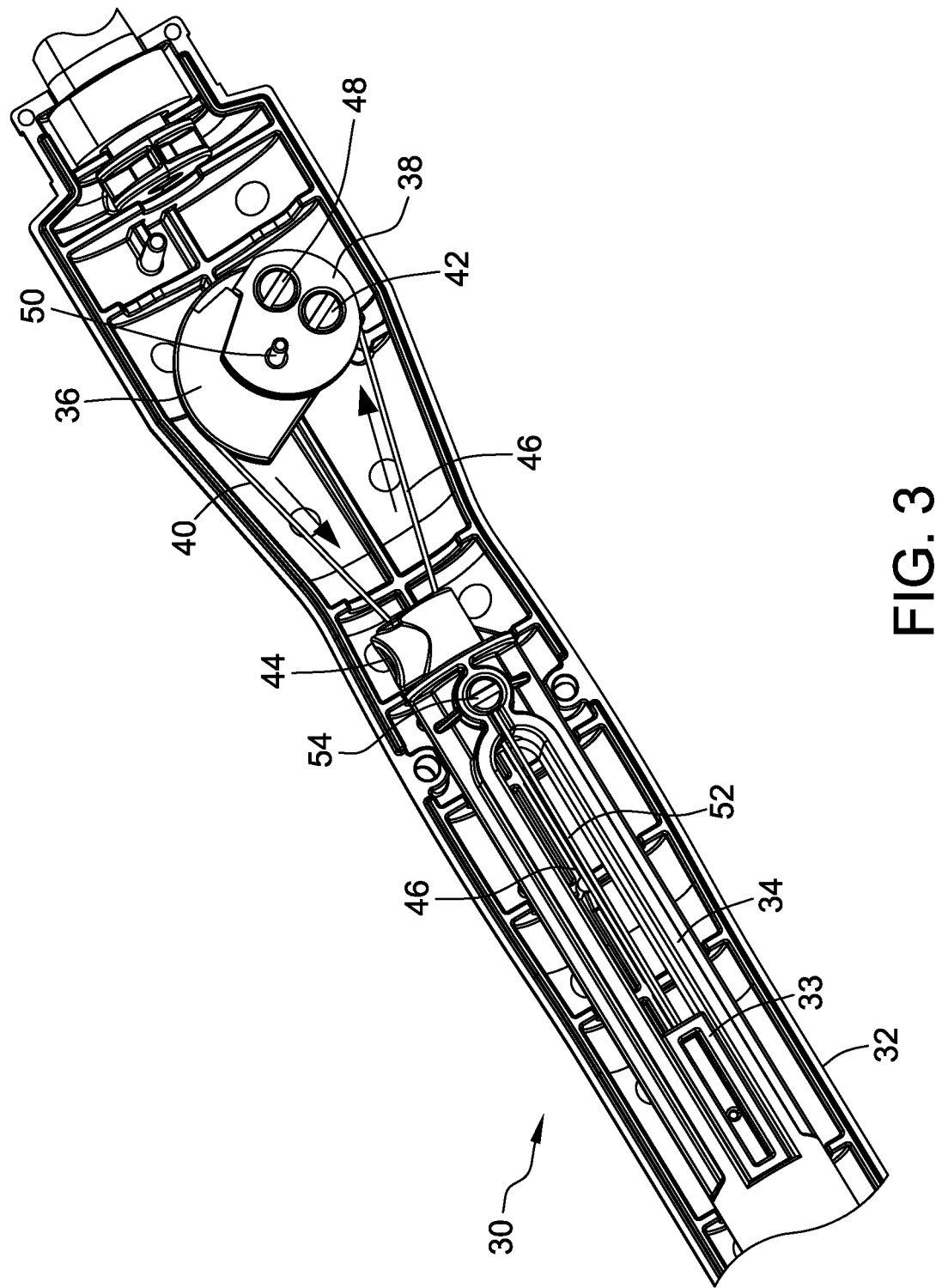
FIG. 3 is a cut-away perspective view of one embodiment of a catheter in accordance with the present disclosure.

In accordance with a number of embodiments of the present disclosure, catheter 10 of FIGS. 1 and 2 may further include an assembly for use in deflecting a portion of distal region 16 of catheter shaft 12. Referring now to FIG. 3, there is shown a plunger-type catheter 30 in a cut-away, perspective view. In this embodiment, catheter 30 includes handle 32, plunger 34, catheter shaft 33, a first rotatable member 36, and a second rotatable member 38. In some embodiments, catheter shaft 33 may be affixed or connected to handle 32 such that plunger 34 moves relative to catheter shaft 33 upon actuation. First rotatable member 36 and second rotatable member 38 are coupled or otherwise affixed together to form a stacked, unitary piece of material wherein second rotatable member 38 sits atop first rotatable member 36. First rotatable member 36 has a first diameter, and second rotatable member 38 has a second diameter wherein the second diameter is smaller than the first diameter (See FIG. 4, discussed below). First rotatable member 36 and second rotatable member 38 are coupled or otherwise affixed together such that a center point of second rotatable member 38 is offset from a center point of first rotatable member 36 (See FIG. 4, discussed below); that is, the center point of second rotatable member 38 is not in direct alignment with the center point of first rotatable member 36 such that a misalignment results.

Referring again to FIG. 3, a first pull wire 40 is coupled to first rotatable member 36 at a first tuning pin 42 and further coupled to plunger 34 at a second tuning pin 44. A second pull wire 46 is coupled to second rotatable member 38 at a third tuning pin 48 and further coupled to a deflectable distal region of catheter 30 (not shown). Set post (or rod) 50 attaches coupled first rotatable member 36 and second rotatable member 38 to catheter 30. Optionally, in some embodiments catheter 30 may additionally include a third pull wire 52, which is coupled to a fourth tuning pin 54 and further coupled to the deflectable distal region of catheter 30 (not shown). This optional third pull wire 52 may be used to further assist in returning the deflected distal region of catheter 30 to straight upon use as described herein. Tuning pins 42, 44, 48, and 54 may be used to secure first pull wire 40, second pull wire 46 and third pull wire 52 as well as optimize and customize the desired tension on first pull wire 40, second pull wire 46, and third pull wire 52 to achieve the desired amount of tension and hence deflection of the distal region of catheter 30.

Figure 4:
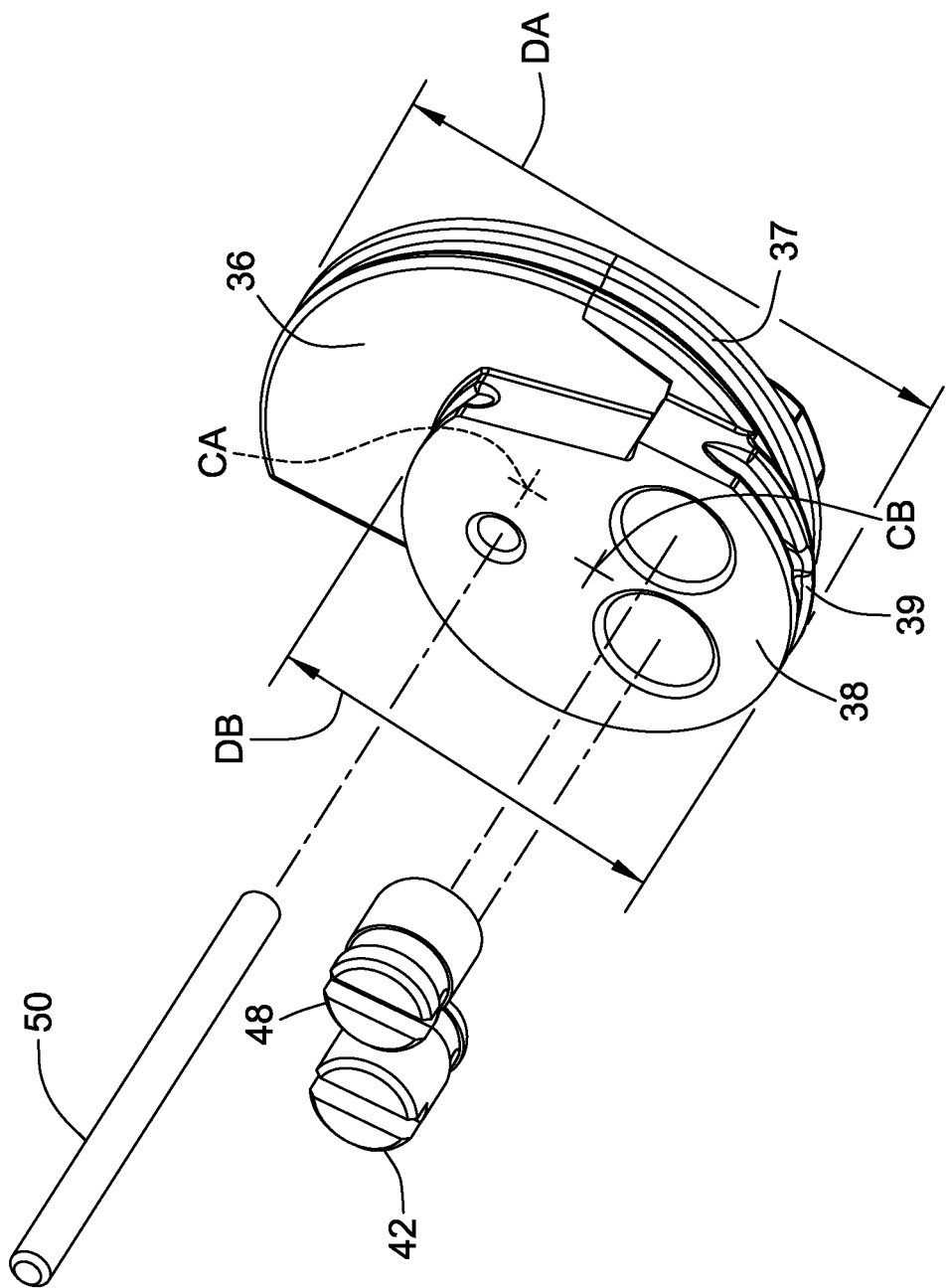
FIG. 4 is an exploded and expanded view of one embodiment of a portion of a catheter in accordance with the present disclosure.

Referring now to FIG. 4, there is shown an expanded and exploded view of a portion of catheter 30 of FIG. 3. FIG. 4 shows first rotatable member 36 coupled to second rotatable member 38 wherein second rotatable member 38 sits atop first rotatable member 36. First rotatable member 36 has an outer surface 37, a diameter DA and center point CA. Second rotatable member 38 has an outer surface 39, a diameter DB and a center point CB. As illustrated in FIG. 4, center point CA of first rotatable member 36 is offset from center point CB of second rotatable member 38 such that first rotatable member 36 and second rotatable member 38 are coupled in an offset center point position. As further illustrated in FIG. 4, diameter DA of first rotatable member 36 is larger than diameter DB of second rotatable member 38. Both diameter DA and diameter DB may have a constant diameter (or constant radius) or may have a varying diameter (or varying radius), depending upon the specific desired embodiment. In some embodiments, one of first rotatable member 36 and second rotatable member 38 may have a constant diameter (or radius) while the other may have a varying diameter (or radius). Diameter DA of first rotatable member 36 may be, in some embodiments, from 0.6 inches to 1.0 inch, or even from 0.7 inches to 0.9 inches, or even 0.8 inches. Diameter DB of second rotatable member 38 may be, in some embodiments, from 0.1 inches to 0.59 inches, or even from 0.4 inches to 0.59 inches, or even 0.58 inches. In one specific embodiment of the present disclosure, diameter DA is about 0.8 inches and diameter DB is about 0.58 inches. Also shown in FIG. 4 is set post 50, first tuning pin 42 and third tuning pin 48, as described above.

First rotatable member 36 and second rotatable member 38 may be constructed of any material of suitable weight and robustness to perform the intended function of the members as described herein and, as such, the selection of material is not critical. In some embodiments, first rotatable member 36 and second rotatable member 38 may be constructed of one or more materials selected from the group consisting of relatively hard and lubricious polymeric materials, such as, but not limited to, acetal homopolymers and copolymers, polycarbonates, polyketones, polyesters, reinforced polyolefins, fluoropolymers, lubricated nylons, or combinations thereof. First rotatable member 36 and second rotatable member 38 may be coupled together using any suitable technique for joining the materials including, for example, a suitable adhesive or other known means. Alternatively, the first rotatable member 36 and second rotatable member 38 may be molded as a single, unitary piece.

First pull wire 40, second pull wire 46, and optional third pull wire 52 may be constructed of any material, or combination of two or more materials, having sufficient strength, stretchability, and durability to perform the intended function of the pull wires as described herein, including both fiber-based materials and metal or metal alloy-based materials, for example. Suitable materials may include, for example, a Kevlar® aramid fiber braided material, a Vectran® fiber, a stainless steel wire, a nickel wire, a nickel alloy wire, or a combination thereof. In some embodiments of the present disclosure a pull wire of one material may be connected or otherwise affixed to a pull wire of a different material such that the resulting pull wire is constructed of a combination of two or more materials. For example, in one specific embodiment, a single pull wire may be comprised of a fibrous material (such as Kevlar® or Vectran®) that is connected (using for example, a suitable crimp, such as a titanium crimp, or other suitable connection means) to a conventional pull wire constructed of stainless steel or another metal or metal alloy material. The portion of this pull wire constructed from the fibrous material may be utilized around the first rotatable member and/or the second rotatable member and the portion of the pull wire constructed of the conventional stainless steel or another metal or metal alloy material may be connected to the distal end of the catheter shaft in order to allow for deflection.

In accordance with the present disclosure, the above-described deflecting assembly may be utilized with a catheter to provide a method of deflecting a distal region of medical device such that the medical device can be suitably used in a medical procedure to navigate the vasculature of an individual. In many embodiments, the actuation forces required for deflection may be less than 7.5 ft/lbs, or even less than 5.0 ft/lbs, or even about 3.5 ft/lbs. The deflecting assembly described herein may be utilized to provide a variable torque to the second pull wire 46 (See FIG. 3) that is coupled to the distal region of the catheter shaft to be deflected, as described herein. As such, in use when the plunger 34 (See FIG. 3) of the catheter 30 is advanced distally, the first pull wire 40 (See FIG. 3) causes rotation of the first rotatable member 36 (See FIG. 3) which in turn causes rotation of the second rotatable member 38 (See FIG. 3 and arrows therein showing directional movement of the first rotatable member 36 and the second rotatable member 38) in the same direction. Because the second rotatable member 38 is coupled to the first rotatable member 36 in an offset center position as described above, and because the diameter of the second rotatable member 38 is smaller than the diameter of the first rotatable member 36, the second pull wire 46 moves from a position farthest away from the center point of the first rotatable member 36 when the deflectable distal region is in a neutral state to a position closer to the center point of the first rotatable member 36 when the deflectable distal region is in a deflected state, thus increasing the torque as the distal region of the catheter shaft is deflected and limiting additional force required by a user to continue deflection of the distal region of the catheter shaft.

In accordance with the present disclosure, by providing a deflecting assembly that utilizes a variable torque on the second pull wire 46 that causes deflection of the distal region of the catheter shaft (that is, an increased torque as the distal region of the catheter shaft is deflected), an increased mechanical advantage may be achieved thereby reducing the amount of overall force required to cause deflection of the distal region of the catheter shaft. Stated another way, the amount of force required by the user does not substantially increase as the actuator is distally advanced through full deflection of the distal region of the catheter shaft.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A medical device comprising:
    a catheter shaft having a proximal end and a deflectable distal region;
    a handle coupled to the proximal end of the catheter shaft, wherein the handle includes a plunger movable relative to the handle along a longitudinal axis; and
    a deflecting assembly comprising:
        a first rotatable member coupled to the plunger via a first pull wire and having a first diameter, wherein a first end of the first pull wire is directly coupled to the first rotatable member and a second end of the first pull wire is directly coupled to the plunger; and
        a second rotatable member coupled to the deflectable distal region via a second pull wire and having a second diameter smaller than the first diameter, wherein a first end of the second pull wire is directly coupled to the second rotatable member and a second end of the second pull wire is directly coupled to the deflectable distal region,
        wherein the second rotatable member is coupled to the first rotatable member such that a center point of the second rotatable member is offset from a center point of the first rotatable member;
    wherein the deflecting assembly is configured such that distal movement of the plunger effects rotational movement in a first direction of the first rotatable member and the second rotatable member, resulting in deflection of the deflectable distal region of the catheter shaft.

2. The medical device of claim 1 wherein the first pull wire is configured to wrap around an outer surface of the first rotatable member and wherein the second pull wire is configured to wrap around an outer surface of the second rotatable member.

3. The medical device of claim 1 wherein each of the first and second rotatable members have a constant diameter.

4. The medical device of claim 1 wherein the first rotatable member is coupled to the second rotatable member via a rod extending through each of the first rotatable member and the second rotatable member.

5. The medical device of claim 1 wherein an end of the second pull wire coupled to the second rotatable member is a first distance from the center point of the first rotatable member when the device is in a neutral position, wherein the end of the second pull wire coupled to the second rotatable member is a second distance from the center point of the first rotatable member when the device is in a deflected position, and wherein the first distance is greater than the second distance.

6. The medical device of claim 1 wherein the first pull wire is coupled to the first rotatable member by a first tuning pin and wherein the second pull wire is coupled to the second rotatable member by a second tuning pin.

7. The medical device of claim 1 wherein the first and second pull wires are formed from a fibrous material.

8. The medical device of claim 1 further comprising a third pull wire coupled at a first end thereof to the deflectable distal region and coupled at a second end thereof to the plunger, wherein the third pull wire is configured to assist in returning the deflectable distal region to a neutral position upon proximal movement of the plunger.

9. The medical device of claim 1 wherein the catheter shaft is coupled to the handle.

10. A method of deflecting a distal region of a medical device, the method comprising:
   providing a medical device comprising:
      a catheter shaft having a proximal end and a deflectable distal region;
      a handle coupled to the proximal end of the catheter shaft, wherein the handle includes a plunger movable relative to the handle along a longitudinal axis; and
      a deflecting assembly comprising:
         a first rotatable member coupled to the plunger via a first pull wire and having a first diameter, wherein a first end of the first pull wire is directly coupled to the first rotatable member and a second end of the first pull wire is directly coupled to the plunger;
         a second rotatable member coupled to the deflectable distal region via a second pull wire and having a second diameter smaller than the first diameter wherein a first end of the second pull wire is directly coupled to the second rotatable member and a second end of the second pull wire is directly coupled to the deflectable distal region;
         wherein the second rotatable member is coupled to the first rotatable member such that a center point of the second rotatable member is offset from a center point of the first rotatable member; and
   distally advancing the plunger with respect to the handle to a position wherein the deflectable distal region of the catheter shaft is in a deflected configuration.

11. The method of claim 10 wherein distally advancing the plunger with respect to the handle to a position wherein the deflectable distal region of the catheter shaft is in a deflected position comprises distally advancing the plunger such that the first pull wire causes rotation of the first rotatable member.

12. The method of claim 11 wherein rotation of the first rotatable member causes rotation of the second rotatable member such that the second pull wire rotates around the second rotatable member.

13. The method of claim 12 wherein rotation of the second pull wire around the second rotatable member causes deflection of the deflectable distal region.

* * * * *